(12) United States Patent
Clarke et al.

(10) Patent No.: US 7,688,440 B2
(45) Date of Patent: Mar. 30, 2010

(54) RAMAN SPECTROSCOPIC TEST STRIP SYSTEMS

(75) Inventors: Richard H. Clarke, Big Sky, MT (US); M. Edward Womble, Austin, TX (US)

(73) Assignee: Prescient Medical, Inc., Doylestown, PA (US)

( * ) Notice: Subject to any disclaimer, the term of this patent is extended or adjusted under 35 U.S.C. 154(b) by 338 days.

(21) Appl. No.: 11/698,084

(22) Filed: Jan. 26, 2007

(65) Prior Publication Data

US 2007/0224683 A1    Sep. 27, 2007

Related U.S. Application Data (63) Continuation-in-part of application No. 11/340,712, filed on Jan. 27, 2006, which is a continuation-in-part of application No. 10/905,956, filed on Jan. 27, 2005, now Pat. No. 7,524,671.

(60) Provisional application No. 60/765,699, filed on Feb. 6, 2006, provisional application No. 60/837,256, filed on Aug. 11, 2006.

(51) Int. Cl.
    *G01J 3/44* (2006.01)
(52) U.S. Cl. ..................................... 356/301
(58) Field of Classification Search ................ 356/301, 356/317–318
    See application file for complete search history.

(56) References Cited

U.S. PATENT DOCUMENTS

| | | |
|---|---|---|
| 3,598,727 A | 8/1971 | Willcock |
| 3,900,396 A | 8/1975 | Lamadrid |
| 4,127,033 A | 11/1978 | Warren et al. |
| 4,172,033 A | 10/1979 | Willcock |
| 4,267,040 A | 5/1981 | Schal |
| 4,329,986 A | 5/1982 | Babb |
| 4,370,983 A | 2/1983 | Lichtenstein |
| 4,573,761 A | 3/1986 | McLachlan et al. |
| 4,733,253 A | 3/1988 | Daniele |
| 4,769,134 A | 9/1988 | Allan et al. |
| 4,781,458 A | 11/1988 | Angel et al. |
| 4,913,142 A | 4/1990 | Kittrell et al. |
| 5,011,284 A | 4/1991 | Tedesco et al. |
| 5,112,127 A | 5/1992 | Carrabba et al. |

(Continued)

FOREIGN PATENT DOCUMENTS

DE        4433305        4/1996

(Continued)

OTHER PUBLICATIONS

Hanlon E.B. et al. "Prospects for in vivo Raman spectroscopy," Phys. Med. Biol 45 (2000) R1-R59.

(Continued)

*Primary Examiner*—Kara E Geisel
(74) *Attorney, Agent, or Firm*—Michele V. Frank; Patton Boggs LLP (57) ABSTRACT

The invention provides diagnostic apparatuses that are advantageously adapted for the Raman spectroscopic analysis of fluid samples, such as biological fluid samples, deposited on test strip substrates. The tests strips may be include a surface-enhanced Raman spectroscopy (SERS) surface for deposition and analysis of a sample and/or may be lateral flow binding assay type test strips.

4 Claims, 8 Drawing Sheets

U.S. PATENT DOCUMENTS

| | | | |
|---|---|---|---|
| 5,139,334 A | 8/1992 | Clarke | |
| 5,199,431 A | 4/1993 | Kittrell et al. | |
| 5,266,498 A | 11/1993 | Tarcha et al. | |
| 5,280,788 A | 1/1994 | Janes et al. | |
| 5,290,275 A | 3/1994 | Kittrell et al. | |
| 5,304,173 A | 4/1994 | Kittrell et al. | |
| 5,318,024 A | 6/1994 | Kittrell et al. | |
| 5,372,135 A | 12/1994 | Mendelson et al. | |
| 5,376,556 A | 12/1994 | Tarcha et al. | |
| 5,377,004 A | 12/1994 | Owen et al. | |
| 5,381,237 A | 1/1995 | Sela | |
| 5,400,136 A | 3/1995 | Vo-Dinh | |
| 5,419,323 A | 5/1995 | Kittrell et al. | |
| 5,439,000 A | 8/1995 | Gunderson et al. | |
| 5,445,972 A | 8/1995 | Tarcha et al. | |
| 5,452,723 A | 9/1995 | Wu et al. | |
| 5,455,673 A | 10/1995 | Alsmeyer et al. | |
| 5,534,997 A | 7/1996 | Schrader et al. | |
| 5,553,616 A | 9/1996 | Ham et al. | |
| 5,562,100 A | 10/1996 | Kittrell et al. | |
| 5,567,628 A | 10/1996 | Tarcha et al. | |
| 5,615,673 A | 4/1997 | Berger et al. | |
| 5,621,522 A | 4/1997 | Ewing et al. | |
| 5,657,404 A | 8/1997 | Buchanan et al. | |
| 5,685,988 A | 11/1997 | Malchesky | |
| 5,693,043 A | 12/1997 | Kittrell et al. | |
| 5,697,373 A | 12/1997 | Richards-Kortum et al. | |
| 5,715,263 A | 2/1998 | Ventrudo et al. | |
| 5,751,415 A | 5/1998 | Smith et al. | |
| 5,773,835 A | 6/1998 | Sinofsky | |
| 5,815,260 A | 9/1998 | Dou et al. | |
| 5,817,007 A | 10/1998 | Fodgaard et al. | |
| 5,842,995 A | 12/1998 | Mahadevan-Jansen et al. | |
| 5,849,179 A | 12/1998 | Emerson et al. | |
| 5,858,186 A | 1/1999 | Glass | |
| 5,862,273 A | 1/1999 | Pelletier | |
| 5,864,397 A | 1/1999 | Vo-Dinh | |
| 5,870,188 A | 2/1999 | Ozaki et al. | |
| 5,902,246 A | 5/1999 | McHenry et al. | |
| 5,902,247 A | 5/1999 | Coe et al. | |
| 5,951,482 A | 9/1999 | Winston et al. | |
| 5,982,484 A | 11/1999 | Clarke et al. | |
| 5,991,653 A | 11/1999 | Richards-Kortum et al. | |
| 5,993,378 A | 11/1999 | Lemelson | |
| 6,018,389 A | 1/2000 | Kyle et al. | |
| 6,038,887 A | 3/2000 | Vild et al. | |
| 6,044,285 A | 3/2000 | Chaiken et al. | |
| 6,064,897 A | 5/2000 | Lindberg et al. | |
| 6,087,182 A | 7/2000 | Jeng et al. | |
| 6,095,982 A | 8/2000 | Richards-Kortum et al. | |
| 6,144,444 A | 11/2000 | Haworth et al. | |
| 6,151,522 A | 11/2000 | Alfano et al. | |
| 6,154,596 A | 11/2000 | Ionov | |
| 6,156,002 A | 12/2000 | Polaschegg et al. | |
| 6,174,291 B1 | 1/2001 | McMahon et al. | |
| 6,208,887 B1 | 3/2001 | Clarke | |
| 6,212,424 B1 | 4/2001 | Robinson | |
| 6,219,137 B1 | 4/2001 | Vo-Dinh | |
| 6,226,082 B1 | 5/2001 | Roe | |
| 6,258,027 B1 | 7/2001 | Sternby | |
| 6,281,971 B1 | 8/2001 | Allen et al. | |
| 6,284,131 B1 | 9/2001 | Hogard et al. | |
| 6,284,141 B1 | 9/2001 | Shaldon et al. | |
| 6,310,686 B1 | 10/2001 | Jiang | |
| H2002 H | 11/2001 | McLachlan et al. | |
| H2202 H | 11/2001 | McLachlan et al. | |
| 6,313,914 B1 | 11/2001 | Roe | |
| 6,373,567 B1 | 4/2002 | Wise et al. | |
| 6,486,948 B1 | 11/2002 | Zeng | |
| 6,507,747 B1 | 1/2003 | Gowda et al. | |
| 6,511,814 B1 | 1/2003 | Carpenter | |
| 6,514,767 B1 | 2/2003 | Natan | |
| 6,560,478 B1 | 5/2003 | Alfano et al. | |
| 6,574,501 B2 | 6/2003 | Lambert et al. | |
| 6,580,935 B1 | 6/2003 | Wach et al. | |
| 6,621,574 B1 | 9/2003 | Forney et al. | |
| 6,643,012 B2 | 11/2003 | Shen et al. | |
| 6,666,840 B1 | 12/2003 | Falkvall et al. | |
| 6,690,966 B1 | 2/2004 | Rava et al. | |
| 6,707,548 B2 * | 3/2004 | Kreimer et al. | 356/301 |
| 6,721,583 B1 | 4/2004 | Durkin et al. | |
| 6,750,065 B1 | 6/2004 | White et al. | |
| 6,750,963 B2 | 6/2004 | Sampas | |
| 6,770,488 B1 | 8/2004 | Carron et al. | |
| 6,841,159 B2 | 1/2005 | Simonson | |
| 6,844,200 B2 | 1/2005 | Brock | |
| 6,897,951 B2 | 5/2005 | Womble et al. | |
| 6,924,153 B1 | 8/2005 | Boehringer et al. | |
| 7,102,746 B2 | 9/2006 | Zhao | |
| 7,245,369 B2 | 7/2007 | Wang et al. | |
| 7,326,576 B2 | 2/2008 | Womble et al. | |
| 7,351,212 B2 | 4/2008 | Roe | |
| 7,374,546 B2 | 5/2008 | Roe et al. | |
| 2003/0105069 A1 | 6/2003 | Robinson et al. | |
| 2003/0231305 A1 | 12/2003 | Zeng | |
| 2004/0116829 A1 | 6/2004 | Raney et al. | |
| 2004/0127789 A1 | 7/2004 | Ogawa | |
| 2004/0127819 A1 | 7/2004 | Roe | |
| 2004/0160601 A1 * | 8/2004 | Womble et al. | 356/301 |
| 2004/0174520 A1 | 9/2004 | Premasiri et al. | |
| 2004/0186394 A1 | 9/2004 | Roe et al. | |
| 2004/0191921 A1 | 9/2004 | Farquharson et al. | |
| 2004/0204634 A1 | 10/2004 | Womble et al. | |
| 2004/0247485 A1 * | 12/2004 | Kraus et al. | 422/82.08 |
| 2005/0059894 A1 | 3/2005 | Zeng et al. | |
| 2005/0105084 A1 | 5/2005 | Wang et al. | |
| 2005/0128476 A1 | 6/2005 | Zhao | |
| 2005/0171436 A1 | 8/2005 | Clarke et al. | |
| 2005/0250141 A1 | 11/2005 | Lambert et al. | |
| 2005/0264808 A1 | 12/2005 | Wang | |
| 2006/0166302 A1 | 7/2006 | Clarke et al. | |
| 2006/0176478 A1 | 8/2006 | Clarke et al. | |
| 2006/0240401 A1 | 10/2006 | Clarke et al. | |
| 2007/0059203 A1 | 3/2007 | Burrell et al. | |
| 2007/0224683 A1 | 9/2007 | Clarke et al. | |
| 2008/0064120 A1 | 3/2008 | Clarke et al. | |

FOREIGN PATENT DOCUMENTS

| | | |
|---|---|---|
| EP | 1846571 | 10/2007 |
| JP | 2007/553245 | 7/2007 |
| WO | WO 1999/010742 | 3/1999 |
| WO | WO 2006/81380 | 8/2006 |
| WO | WO 2007/089540 | 8/2007 |
| WO | WO 2007/089551 | 8/2007 |
| WO | WO 2007/092173 | 8/2007 |

OTHER PUBLICATIONS

Premasiri, W. Ranjith et al. "Urine Analysis by Laser Raman Spectroscopy," Lasers in Surgery and Medicine 28 (2001) pp. 330-334.

Clarke, R.H. et al. "Low-resolution Raman Spectroscopy as an Analytical Tool for Organic Liquids," Spectroscopy 13 (Oct. 1998) pp. 28-35 (downloaded on Jul. 31, 2003 from www.oceanoptics.com/products/ramanarticle.asp).

Clarke R.H. et al. "Low-Resolution Raman Spectroscopy: Instrumentation and Applications in Chemical Analysis," Journal of Raman Spectroscopy 30 (1999) pp. 827-832.

Berger, Andrew Joshua. "Measurement of analytes in human serum and whole blood samples by near-infrared Raman spectroscopy," Ph.D. Dissertation, Massachusetts Institute of Technology, Jun. 1998.

Berger, Andrew J. et al. "MUlticomponent blood analysis by near-infrared Raman spectroscopy," Applied Optics 38:13 (May 1, 1999) pp. 2916-2926.

"RamanProbe" brochure published by InPhotonics (no publication date available).

Womble, M. Edward et al. "Low-Resolution Raman Method Offers Low Cost and Portability," Laser Focus World (Apr. 1999) pp. 131-136.

Bao et al., Anal Chem 2004; 76(15) 4531-4536.

International Search Report, PCT/US2007/002106, dated Apr. 7, 2008.

Berger, A. J. et al., "Feasibility of measuring blood glucose concentration by near-infrared Raman spectroscopy," Spectrochimica Acta Part A, 1997; 53:287-292.

Berger, A. J. et al., "Rapid, noninvasive concentration measurements of aqueous biological analytes by near-infrared Raman spectroscopy," Applied Optics, 1996, 35(1):209-212.

Brennan, J. F. et al., "Histochemical Analysis of Human Coronary Artery Using Near-Infrared Raman Spectroscopy," Proc. Of SPIE; 1994; 2324:98-102.

Goodridge, C.F. "Rapid on-site cyanide assay for blood and saliva samples", Database: Toxcenter, DN Crisp-2003-GM68246-01; 2004, Abstract.

International Search Report, PCT/US2007/002108, dated Nov. 20, 2007.

International Search Report, PCT/US2007/02062, dated Sep. 11, 2007.

Kneipp, K. et al., "Near-infrared surface-enhanced Raman scattering (NIR-SERS) of neurotransmitters in colloidal silver solutions," Spectrochimica Acta, 1995; 51(A)(3): 481-487.

Liistro, F. et al., "First Clinical Experience With a Paclitaxel Derivate-Eluting Polymer Stent System Implantation for In-Stent Restenosis: Immediate and Long-Term Clinical and Angiographic Outcome," Circulation, 2002; 105, 1883-1886.

Morice, M. et al., "A Randomized Comparison of a Sirolimus-Eluting Stent with a Standard Stent for Coronary Revascularization," N. Engl. J. Med., 2002; 346(23):1773-1780.

Sharma, S. et al., Correction "Sirolimus-Eluting Coronary Stents," N. Engl. J. Med., 2002; 347:1285.

Nave, S.E., "Rugged Fiber Optic Probes and Sampling Systems for Remote Chemical Analysis Via the Raman Technique," Advances in Instrumentation and Control, 1996; 51:453-467.

Qu, J. Y. et al, "Rapid quantification of the clinically important analytes in sub-µI simulating human sera," Proc. Of SPIE, 2000, 3918:174-180.

Römer, T. J. et al., "Histopathology of Human Coronary Atherosclerosis by Quantifying Its Chemical Composition with Raman Spectroscopy," Cirulation 1998; 97:878-885.

Schultz, C. P. et al, "A Comparison of Non-destructive and Non-invasive material depth profiling using FT-Raman fiber optics and microspectroscopy," Proc. Of SPIE, 2000; 4129:284-293.

Serruys, P.W. et al., "Intravascular Ultrasound Findings in the Multicenter, Randomized, Double-Blind RAVEL (Randomized study with the sirolimus-eluting Velocity balloon-expandable stent in the treatment of patients with de novo native coronary artery Lesions) Trial," Circulation, 2002, 106:798-803.

Shim, M.G. et al, "Evaluation of fiber optic probes for in vivo Raman spectroscopy," SPIE, 1998; 3257:208-217.

Walker, P.A. III et al., "Capillary isotachophoresis with fiber-optic Raman spectroscopic detection Performance and application to ribonucleotides," Journal of Chromatography A, 1998; 805:269-275.

Williams, K.P.J., "Remote Sampling Using a Fibre-Optic Probe in Fourier Transform Raman Spectroscopy," Journal of Raman Spectroscopy, 1990; 21: 147-151.

Zimba, C.G. et al., "FT-Raman Spectroscopy with Fiber-Optic Probes and a Diode-Bar-Pumped Nd:YAG Laser," Applied Spectroscopy, 1991; 45: 162-165.

* cited by examiner

RAMAN SPECTROSCOPIC TEST STRIP SYSTEMS

This application is a continuation-in-part of U.S. application Ser. No. 11/340,712 filed Jan. 27, 2006 which is a continuation-in-part of U.S. application Ser. No. 10/905,956 filed Jan. 27, 2005, each of which is incorporated by reference herein in its entirety. This application also claims the benefit of U.S. application Ser. Nos. 60/837,256 filed Aug. 11, 2006 and 60/765,699 filed Feb. 6, 2006, each of which is incorporated by reference herein in its entirety.

FIELD OF THE INVENTION

The invention relates generally to diagnostic apparatuses for the optical interrogation of test strips by Raman spectroscopy.

BACKGROUND OF INVENTION

U.S. Pat. Nos. 5,376,556, 5,266,498, 5,445,972 and 5,567,628, each of which is incorporated by reference herein in its entirety, each describe a quantitative, lateral flow test strip system in which the beads/particles have a separate Raman-active label, in addition to an analyte-binding element, such as an antibody.

U.S. Pat. No. 6,514,767, which is incorporated by reference herein in its entirety, describes the preparation of beads having encapsulated Raman tags or "bar codes," to which other molecules can be conjugated.

U.S. Pat. No. 6,750,065, which is incorporated by reference herein in its entirety, describes immunoassays involving surface-enhanced Raman scattering that are based on the displacement of a Raman label molecule.

U.S. Pat. No. 6,844,200, which is incorporated by reference herein in its entirety, describes devices for carrying out lateral-flow assays involving more than one analyte that are not based on Raman spectroscopy.

U.S. Pat. No. 6,924,153, which is incorporated by reference herein in its entirety, describes quantitative lateral flow assays and devices that are not based on Raman spectroscopy.

U.S. Publication No. 20040116829, which is incorporated by reference herein in its entirety, describes sampling devices and methods using a horizontal capillary test strip that may employ Raman spectroscopy.

U.S. Publication No. 20040127819, which is incorporated by reference herein in its entirety, describes blood acquisition suspension system that may employ Raman spectroscopy.

U.S. Publication No. 20040186394, which is incorporated by reference herein in its entirety, describes integrated lancing test strip that may employ Raman spectroscopy.

U.S. Publication No. 20040191921, which is incorporated by reference herein in its entirety, describes simultaneous chemical separation and surface-enhanced Raman spectral detection.

U.S. Publication No. 200502500141, which is incorporated by reference herein in its entirety, describes multiplex lateral flow immunoassays that utilize a quantum dot-based labeling and detection system which are not based on Raman spectroscopy.

SUMMARY OF INVENTION

One embodiment of the invention provides a Raman spectroscopy system that includes: an optical assembly defining an input path and an output path, wherein the input path includes at least one light directing element that receives excitation radiation from a light source and directs it to a sample and the output path further includes at least one light collecting element that collects radiation scattered by the sample for analysis, wherein the input and output paths of the optical assembly are at least substantially orthogonal and the optical assembly further includes a dichroic mirror that directs the excitation radiation to the sample by reflection and transmits scattered radiation returning from the sample to the output path; and a fluid sample, such as a body fluid sample, test substrate-receiving structure for receiving a fluid sample test substrate, which may be standardized and which may be a body fluid sample test substrate, and positioning said substrate for optical interrogation via the optical assembly.

A related embodiment of the invention provides a Raman spectroscopy system that includes: an input fiber through which radiation can propagate to irradiate a sample; a collection fiber through which radiation scattered by the sample can be coupled to a detector; an optical assembly defining an input path and an output path, wherein the input path comprises at least one light directing element that receives excitation radiation from the input fiber and directs it to the sample and the output path further includes at least light collecting element that collects radiation scattered by the sample and couples the scattered radiation into the collection fiber; the input and output paths of the optical assembly are at least substantially orthogonal and the optical assembly further comprises a dichroic mirror that directs the excitation radiation to the sample by reflection and transmits scattered radiation returning from the sample to the output path; and a fluid sample, such as a body fluid sample, test substrate-receiving structure for receiving a fluid sample test substrate, which may be standardized, and positioning said substrate for optical interrogation via the optical assembly.

The fluid sample test substrate receiving structure may include a slot for insertion of the substrate and a guiding channel into which the substrate is inserted. Thus, the fluid sample test substrate-receiving structure may be a test strip-receiving structure. In another variation of the embodiments, the fluid sample test substrate is a test strip. The test strip may be a lateral flow binding assay test strip. The test strip may include a non-mobile surface enhanced Raman spectroscopy substrate. The fluid sample test substrate receiving structure, which may be a test strip receiving structure, and the substrate may be mutually adapted to alignedly position the substrate for optical interrogation by the system.

In one variation, the optical assembly further includes a beam energy dump for absorbing radiation from the input path that is not reflected by the dichroic mirror.

Another embodiment of the invention provides a method for evaluating a fluid sample by Raman spectroscopy, that includes the steps of: depositing a fluid sample, such as a body fluid sample, on a test strip; inserting the test strip into a Raman spectroscopy system according to the invention, wherein the system irradiates at least one part of the test strip to generate a Raman spectra; and wherein the system analyzes at least part of the Raman spectra.

The test strip may include a SERS active substrate in a sample deposition area and the system irradiates the sample deposition area to generate the Raman spectra. The test strip may alternatively or additionally be a lateral flow binding assay test strip including a mobile phase and the system irradiates one or more test stripes and optionally one or more control stripes of the test strip. The mobile phase may include SERS-active particles. The SERS-active particles may include gold beads and/or gold-coated beads.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

DETAILED DESCRIPTION

The invention provides Raman spectroscopy systems that are adapted to receive and read at least substantially planar sample substrates such as test strips and that include an advantageously configured optical assembly by which the sample substrates are optically interrogated.

The invention is further described below with reference to the appended figures. The numeric designation of elements in each figure is not necessarily consistent between figures.

Figure 1:
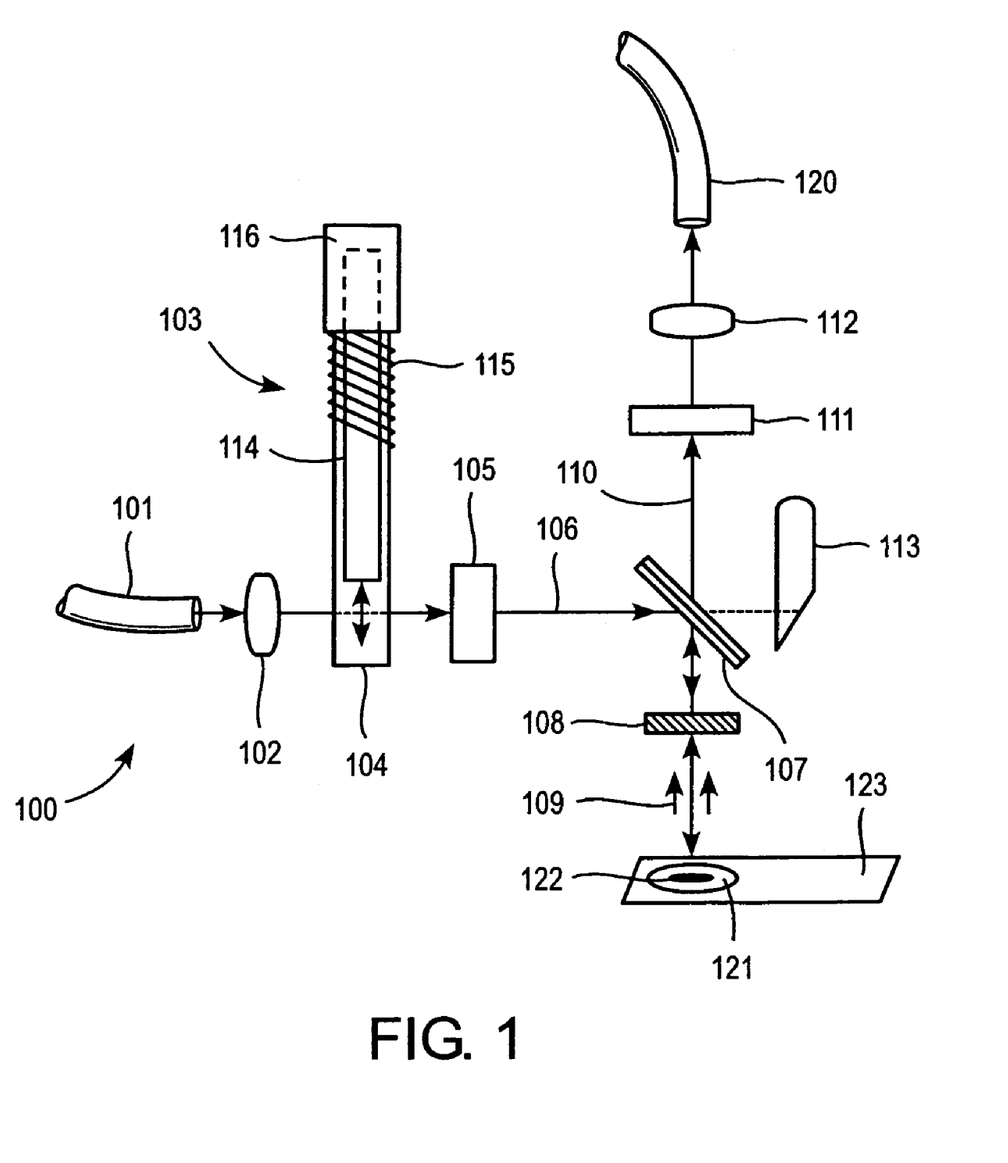
FIG. 1 is a schematic diagram of an optical assembly that may be used in systems according to the invention for the optical interrogation of test substrates.

In one embodiment, an optical assembly 100 as illustrated schematically in FIG. 1 is provided and can be used to perform Raman analyses of test substrates such as test strips. Optical assembly 100 directs the light received from the spectroscopic components into position for contacting the sample, collects the scattered radiation, and returns the collected radiation for analysis. Excitation radiation enters optical assembly 100 via optical fiber 101. The beam from the input fiber is passed through lens 102, which serves to collimate or otherwise project the incoming radiation along beam path 106 with minimal dispersion. The radiation from lens 102 then passes through an optional safety switch 103 including chamber 104 and through one or more optional filters 105, e.g., a low-pass filter.

The filtered incoming light along path 106 is then reflected by dichroic mirror 107 (which may be designed or selected to reflect at nearly all of the excitation light, at least about the desired excitation wavelength) and directed toward target area 121. A second lens 108 may be disposed to focus the excitation radiation to a particular point or region within a sample 122. Lens 108 may generally focus the light on target area 121.

Returning radiation 109 passes through lens 108, which now serves to collimate the scattered radiation and convey it to collection fiber 120. From lens 108, the collected radiation travels along beam path 110, passing through dichroic beamsplitter 107 and, optionally, a mid-pass or long-pass filter 111 and lens 112. Lens 112 serves to focus the collected radiation into output fiber 120. (It should be appreciated that the lens elements of the present invention can be simple or compound lens assemblies and that the functions that these optical elements perform—directing excitation radiation into a sample and collecting scattered radiation for analysis—can be achieved by various equivalent structures, such as those known in the art.)

Optical assembly 100 can further include a "beam dump" 113 to capture and absorb incoming radiation that is not reflected by dichroic mirror 107. Beam dump 113 is optional and may comprise a chamber that has been coated with suitable radiation absorbing material or otherwise formed or shaped to ensure that the radiation that is not directed into the sampling tube is captured and dissipated as heat.

Safety switch 103 is formed by a protective shutter, as shown in FIG. 1, that is disposed in chamber 104. Chamber 104 intersects incoming beam path 106. Plunger 114 is disposed within chamber 104 and operatively connected to spring 115 and solenoid 116. In an activated state, solenoid 116 pulls plunger 114 out of light beam path 106, thereby allowing the multimode radiation to pass through optical assembly 100 and to sample 122. In a deactivated state, ("laser blocking" position), the solenoid releases plunger 114, which moves into light beam path 106 and prevents the multimode radiation from passing to the outside environment. Thus, safety switch 103 ensures that the probe remains in a "normally-off" state should a malfunction or power loss occur.

A handheld or otherwise portable Raman device according to the present invention may additionally include a disposable test strip 123 on which the sample material 122 is deposited.

Figure 2:
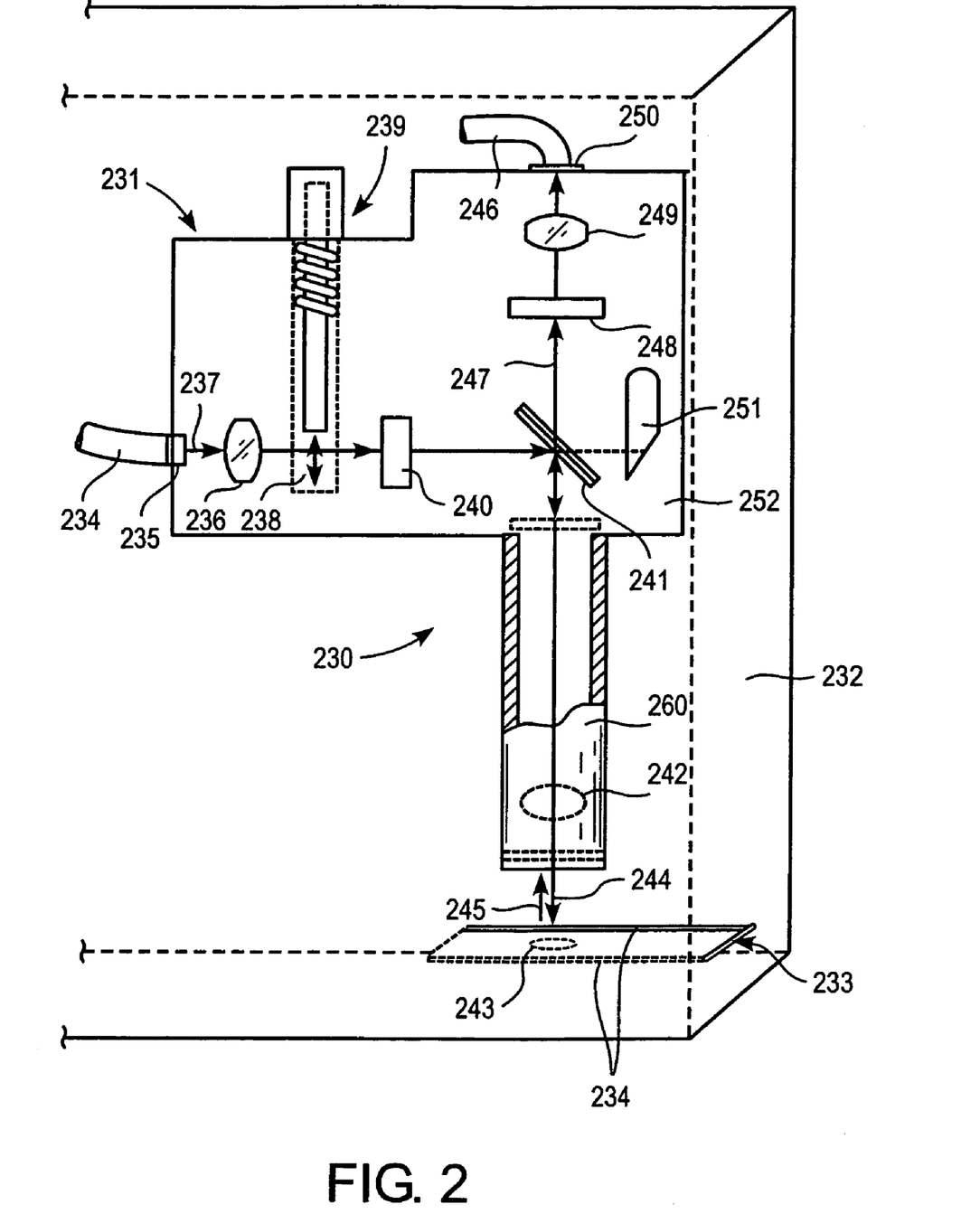
FIG. 2 is a partial cross-sectional schematic diagram of an optical head assembly and housing adapted for optically interrogating test substrates, according to the invention.

FIG. 2 is a schematic diagram of a probe 230 including an optical head assembly 231 having a similar optical configuration as shown in FIG. 1 secured in a housing 232 which is adapted to receive a test strip for optical interrogation by the probe 230. Housing 232 has a slot 233 opening into a channel 234 each being sized and configured to receive an elongate test strip. Probe 230 as shown has a sampling tube 260. However, sampling tube 260 is optional as the optical head and test strip receiving structure may also be configured to cooperate without the use of a sampling tube. Excitation radiation, e.g., from a light source, enters the head assembly as in FIG. 1. The input fiber 234 may be coupled to the head assembly 231 via a coupler 235. The beam from the input fiber is passed through lens 236, which serves to collimate or other project the incoming radiation through the optical head assembly along beam path 237 with minimal dispersion. The radiation from the lens 236 then passes through chamber 238 of the safety switch 239. The incoming beam then passes through one or more optional filters 240, e.g., a low-pass filter.

The filtered incoming light is then reflected by dichroic mirror 241 (which is designed to reflect nearly all of the excitation light) and directed into the sampling tube 260. Within sampling tube 260, a second lens 242 may be disposed to focus the excitation radiation to a particular point or target region 243 on an inserted test strip.

The sampling tube 260 also serves to collect radiation scattered by a sample in response to the excitation beam 244.

The returning radiation 245 passes through lens 242 which now serves to collimate the scattered radiation and convey it to collection fiber 246. From the lens 242, the collected radiation travels along beam path 247, passing through dichroic mirror 241 and, optionally, a mid-pass or long-pass filter 248 and lens 249. Lens 249 serves to focus the collected radiation into the output fiber 246 via output coupler 250.

The optical head assembly 231 may further include a "beam dump" 251 as in FIG. 1. The safety switch 239 may be configured and function as described as in FIG. 1.

As shown in FIGS. 1 and 2, the input and output paths are at least substantially orthogonal. Probe assemblies such as those disclosed in U.S. Pat. No. 6,897,951, which is incorporated by reference herein in its entirety, may be adapted for use in the systems of the present invention.

Figure 3:
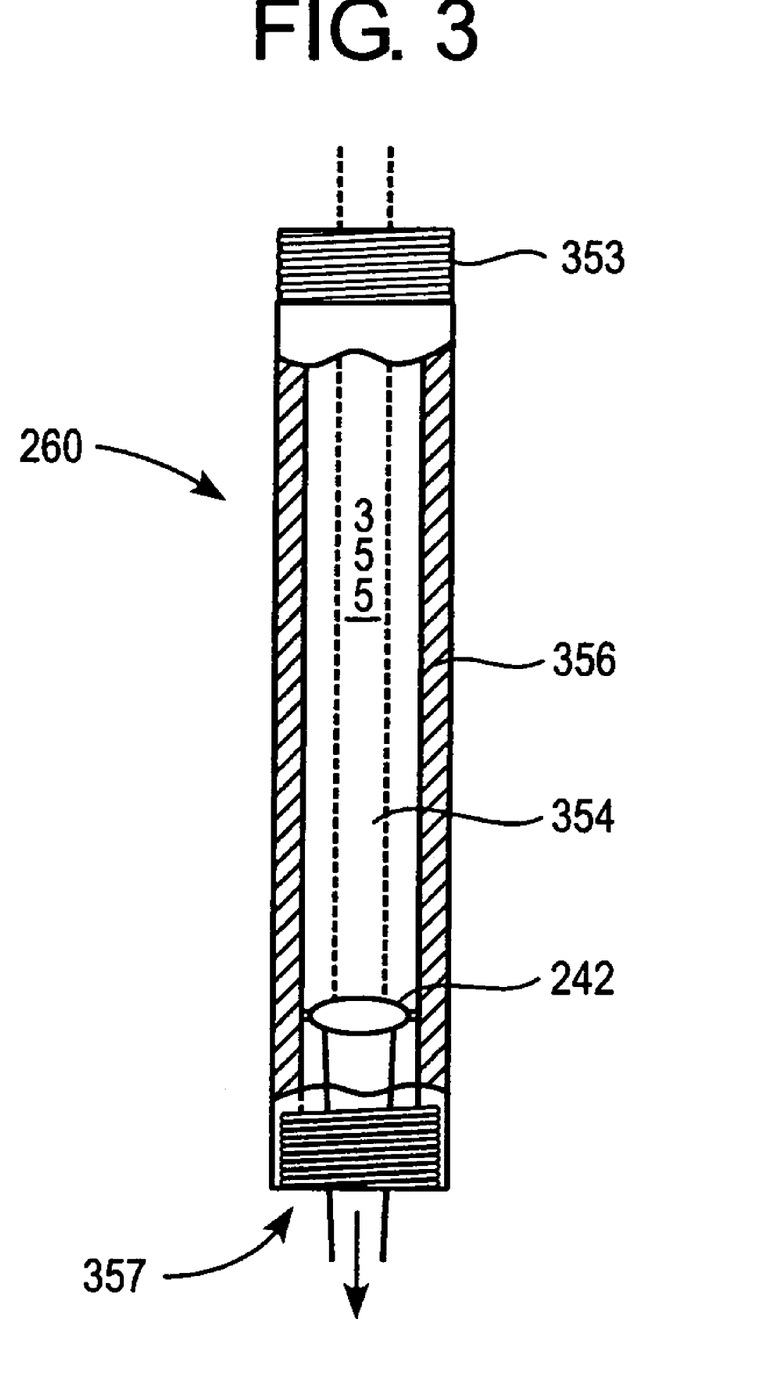
FIG. 3 is a partial cross-sectional schematic view of a sampling tube according to the invention.

In FIG. 3, sampling tube 260 is shown in more detail. The tube 260 can include an externally threaded portion 353 that mates with an internal threaded recess in the block 252 of the optical head assembly 230, as shown in FIG. 2. Block 252 may, for example, be formed aluminum. Sampling tube 260 may be hollow and include an inner passageway 354 which is sufficiently wide so that both the incoming excitation beam and radiation collected from the sample (collectively, shown as the beam path 355) can propagate through the tube with minimal interaction with the tube walls 356. As noted above, lens 242 disposed in the sampling tube serves to both focus the excitation radiation and/or otherwise relay the collected radiation propagating through the tube. The sampling tube may have a distal, sampling end window composed for example of glass or quartz (not shown) that seats into internally threaded portion 357.

Figure 4:
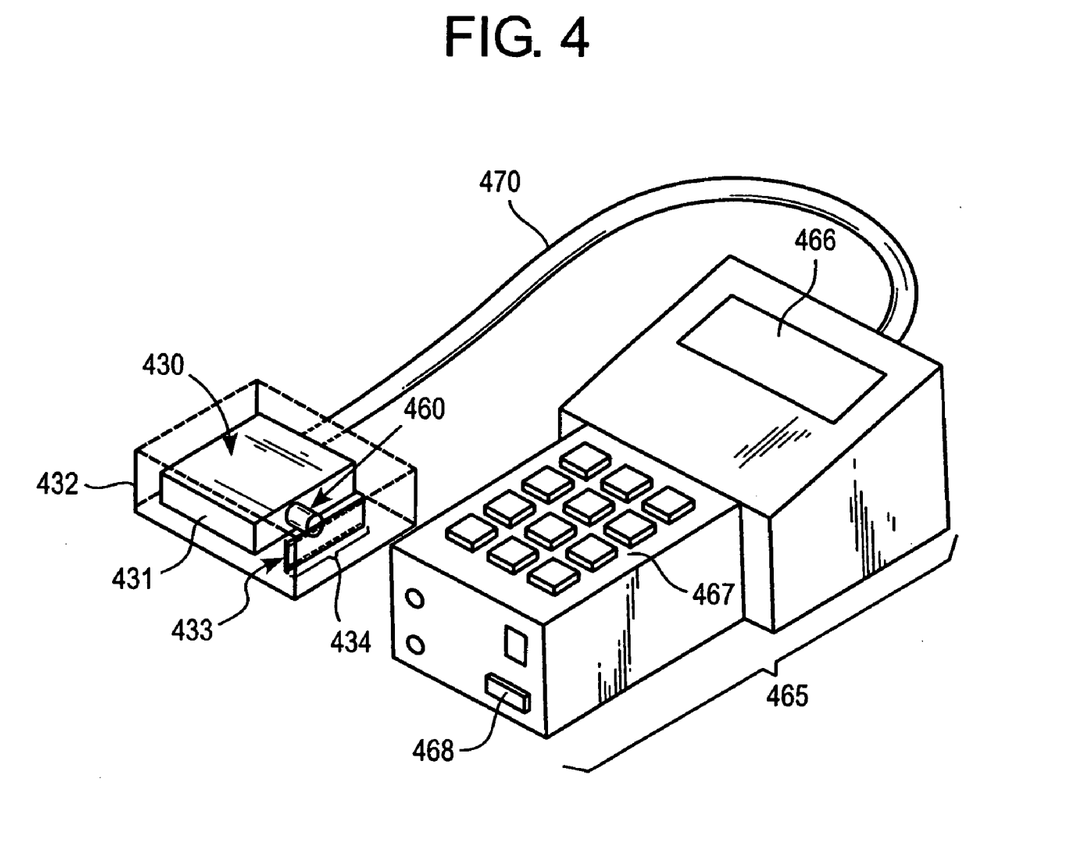
FIG. 4 is an overall schematic view of a portable Raman spectroscopy system embodiment of the invention that is adapted for interrogating tests strips.

FIG. 4 shows an overall Raman spectroscopy system for the analysis of test strips that includes a probe section 430 with its optical head assembly 431 and sampling tube 460 secured in a housing 432 which includes a test strip receiving slot 433 and test strip guiding channel 434, as well as a handheld or otherwise portable analyzer/laser assembly 465. The system shown includes a handheld instrument 465 having a display 466, a keyboard or other user interface 467, and one or more communication ports 468 for receiving or downloading data from other sources. Input and output optical fibers are housed in a flexible conduit 470.

A general system embodiment of the invention includes a test substrate-receiving structure such as a test strip-receiving structure; an optical assembly as described, for example, one having at least substantially orthogonal input and output paths that mediates delivery of excitation light, for example, from a laser light source of the system, to at least one target area of the test substrate (when inserted into the receiving structure) and that mediates delivery of at least some of the Raman spectra light resulting from the irradiation to a detector that detects wavenumber-shifted light; and a processor that analyzes the detected light to provide an quantitative and/or qualitative characterization of at least one analyte in the sample. By processor it is meant a microprocessor system including a microprocessor and whatever computer readable memory and computer instructions may be necessary to carry out processor controlled tasks/calculations. The system may also include at least one output device such as a display and/or a printer to report the results of a test performed using the system. The system may also include an input device such as a keyboard or keypad for programming the system or providing the system with instructions or otherwise controlling the system.

Figure 5:
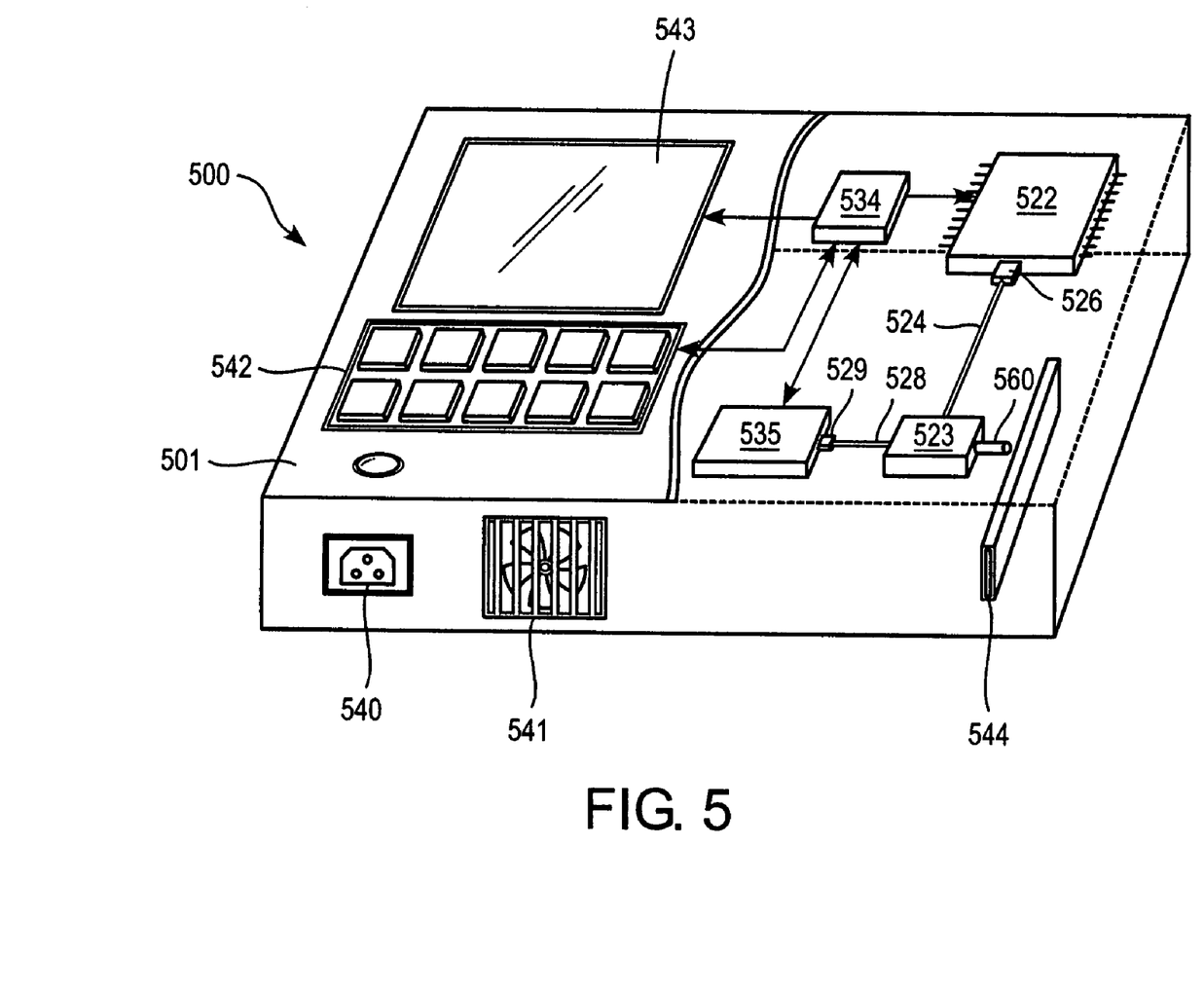
FIG. 5 is an overall schematic view of a portable Raman spectroscopy system embodiment of the invention that is adapted for interrogating tests strips, in which all of the systems components are disposed within a single housing.

FIG. 5 shows an overall Raman spectroscopy system 500 that may be used perform sampling operations on test substrates such as test strips according to the invention and which similar to that of FIG. 4, except that all of the components are housed within a single housing 501. System 500 includes a processor 534 that controls a display 543 and a laser 522, receives input from a keyboard 542 and receives and analyzes input from an onboard Raman spectroscopic element 535. System 500 includes a multi-mode laser source 522 and optional relay optics 526 connected to an excitation optical fiber 524 that carries the laser light to an optical probe head 523 that includes a sampling tube 560 so that excitation light can be directed to (and scattered light received back from) a test strip substrate inserted into test strip-receiving channel 544. The laser source 522 may be one of many multi-mode laser sources. For example, the B&W Tek multi-mode laser BWF-OEM-785-0.5, available from B&W Tek, Inc., of Newark, Del., can be used as the multi-mode laser. Alternatively, for higher resolution, the laser source may be a feedback-stabilized multi-mode laser diode such as a volume Bragg grating (VBG)-stabilized multi-mode laser diodes (available from PD-LD, Inc., Pennington, N.J.) or a single-mode laser, such as those known in the art. The Raman scattered light is collected via the sampling tube 560 and the optical probe head 523 and delivered via flexible optical fiber 528 and optional relay optics 529 to a Raman spectroscopic element 535 of the system. The Raman spectrometer element may, for example, be a low-resolution or high-resolution Raman spectrometer element. System 500 may also be generally provided with a power supply 540 and a cooling fan 541.

Figure 6:
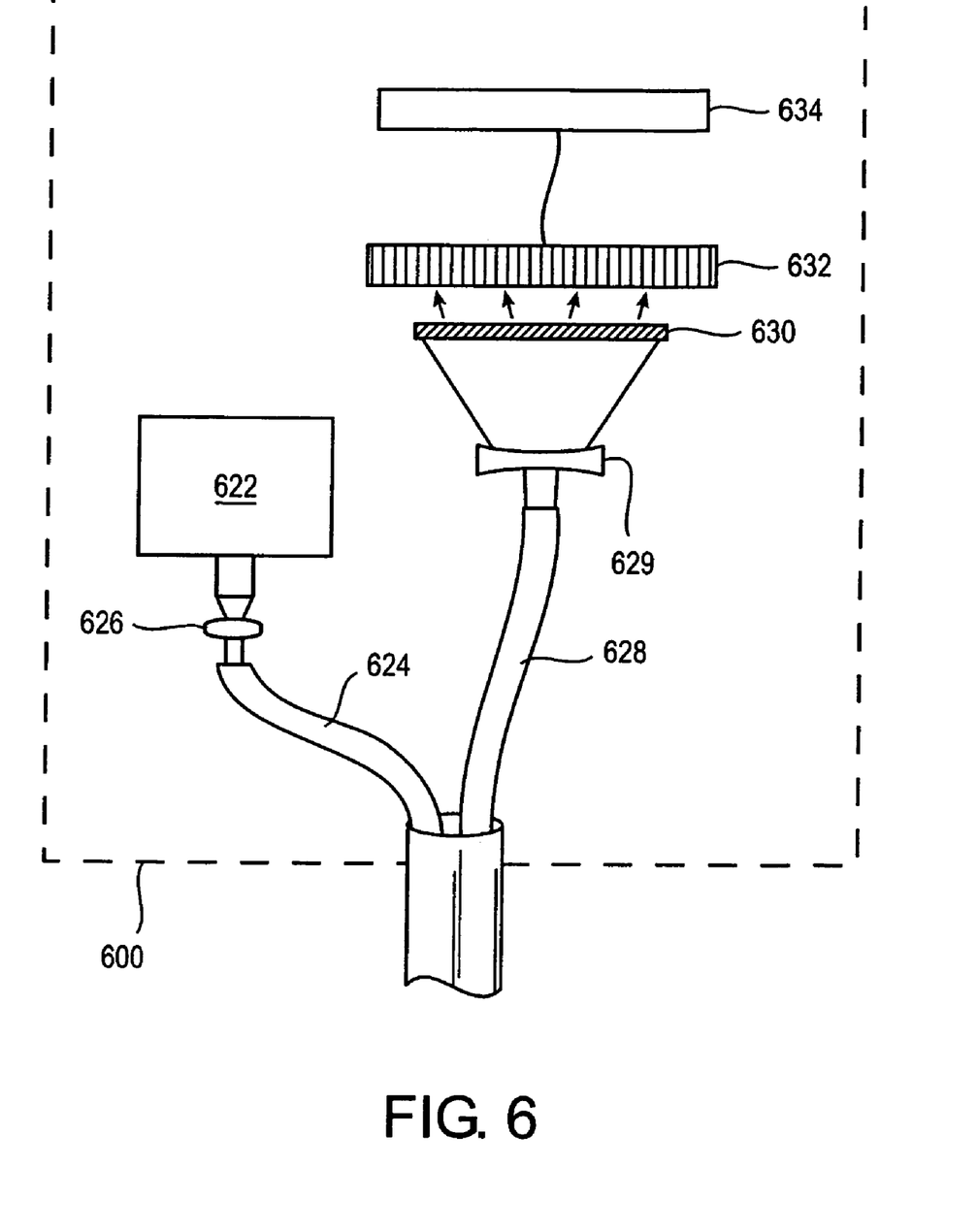
FIG. 6 is a block diagram of a laser/analyzer assembly for a Raman spectroscopy system according to the invention.

A more detailed example of spectroscopic components for system 500 is provided in FIG. 6, which schematically shows a low-resolution Raman spectroscopy apparatus 600 that includes a laser source 622, such as a multi-mode diode laser, and optical fiber 624 connected to the laser source for carrying laser light to the sampling site. Relay optics 626 can optionally be used with the optical fiber to focus and direct the radiation. A person skilled in the art will appreciate that optical fiber 624 may include a variety of optical fibers and light carrying materials that can collect and direct radiation. Light is preferably directed by optical fiber 624 to the sampling area via the optical probe, and after encountering a sample, such as a body fluid sample, is returned in a second optical fiber 628. The returned radiation is directed through dispersion element 630 that serves to disperse the scattered light into different wavelength components. Optional relay optics 629 may be provided between optical fiber 628 and dispersion element 630. The dispersed scattered light is detected by photodetector array 632 that, in this case, consists of a photodiode array or a charged-coupled device (CCD) array. The signals generated by detector array 632 in response to the scattered light are then sent to microprocessor 634 for analysis.

In a low-resolution Raman spectroscopy embodiment, specific spectral bands of interest may be measured at low resolution to obtain the integrated band intensities. These bands can be narrow ones. The resolving power of the dispersion device 630 determines the position of specific wavelengths in the diode array in such a way that the signal from a particular diode in the array will typically correspond to the same (or a similar) narrow range of wavelengths. The combination of the low-resolution dispersion device 630 and the diode array photodetector 632 thus form a spectrometer. The microprocessor 634 may select a particular diode (or diodes) of the array 632 according to the property to be measured. The integrated signals lying in the two ranges can be arithmetically divided to form intensity ratios. The microprocessor 634 may compare these ratios with known values or a correlating function to obtain an estimate of the chemical constituent or property of interest.

A high-resolution Raman spectrometer element may be used if higher resolution is desired.

As an additional safety feature in systems of the invention such as those shown in FIGS. 4 and 5, a switch or detector may be provided that directly or indirectly prevents laser activation when a test substrate, such as a test strip is not inserted into the test substrate-receiving slot/channel. In addition, or alternatively, the slot may be provided with a hingable, self-closing slot door that at least substantially blocks light transmission through the slot when a test substrate, such as a test strip is not interested into the test substrate-receiving slot/channel.

The terms "radiation" and "light" are herein utilized interchangeably. In particular, the term "light" can refer to radiation having wavelength components that lie in the visible range of the electromagnetic spectrum, or outside the visible range, e.g., the infrared or ultraviolet range of the electromagnetic spectrum. In certain embodiments of Raman spectroscopy, the preferred excitation wavelengths will range from about 700 nanometers to 2.5 micrometers. Although this portion of the electromagnetic spectrum is commonly known as infrared (IR) radiation, the term "light" will be used as shorthand expression in describing the path of this radiation as well as the various wavelengths of radiation induced by Raman scattering and collected for analysis.

The systems of the invention can be implemented with any suitable sort of Raman spectroscopy. For example, high-resolution Raman systems as well as low-resolution Raman systems may be used. Information about Raman spectral analysis can be found in U.S. Pat. No. 5,139,334, which is incorporated herein by reference in its entirety and which teaches a low-resolution Raman analysis system for determining certain properties related to hydrocarbon content of fluids. The system utilizes a Raman spectroscopic measurement of the hydrocarbon bands and relates specific band patterns to a property of interest. U.S. Pat. No. 5,982,484, which is incorporated by reference herein in its entirety, teaches sample analysis using low-resolution Raman spectroscopy. U.S. Pat. No. 6,208,887, which is incorporated herein by reference in its entirety, teaches a low-resolution Raman spectral analysis system for determining properties related to in vivo detection of samples based on a change in the Raman scattered radiation produced in the presence or absence of a lesion in a lumen of a subject. U.S. Pat. No. 6,643,012 entitled "Apertureless near-field scanning Raman microscopy using reflection scattering geometry," U.S. Pat. No. 6,095,982 entitled "Spectroscopic method and apparatus for optically detecting abnormal mammalian epithelial tissue," U.S. Pub. No. 20040174520 entitled "Low resolution surface enhanced Raman spectroscopy on sol-gel substrates," U.S. Pub. No. 20040204634 entitled "Raman spectroscopic monitoring of hemodialysis," U.S. Pub. No. 20050171436 entitled "Raman spectroscopy for monitoring drug-eluting medical devices," and U.S. Pub. No. 20050128476 entitled "Raman spectroscope" are each also incorporated by reference herein in their entireties.

Optical fibers that may be utilized in the apparatus of the invention may be multimode fibers, which are available from several commercial sources including, for example, Fiberguide, Inc. of Sterling, N.J. Their diameters may, for example, range from 1 micron to 1000 microns, such as from about 100 microns to about 400 microns, for example, from about 100 microns to about 200 microns. Single fibers and/or fiber bundles may be utilized in the present invention.

The various housings and sampling tubes may, for example, be constructed from various metallic materials, for example, aluminum, steel, copper or titanium and/or may be made from a rigid polymer. Hastalloy and/or stainless steel may, for example, be used.

The diameter of the sampling tube structure is selected such that it enables multi-mode radiation to pass through to the sample, and scattered radiation to pass from the sample without contacting the walls of the tubular structure. For example, the inner diameter of the sampling tube may range from about 3 mm to about 9 mm, such as from about 5 mm to about 6 mm. The outer diameter of the sampling tube may range from about 10 mm to about 25 mm.

Raman measurements may be made in a number of ways in the implementation of the present invention, for example, by comparing the characteristic Raman lines in a spectrum of a sample, with the number of characteristic lines with the standard spectra. Another example includes comparing the ratio of intensities of two characteristic Raman lines which are common in the spectra for a particular constituent with the respective ratios with a standard of that constituent. The correlation of a previously stored spectrum may be used to determine whether the spectrum of the scattered Raman radiation is similar, and the resulting comparison may, for example, be displayed in an alphanumerical form by the microprocessor.

A substantially planar substrate for Raman interrogation may be provided in any shape. In a preferred embodiment, the test substrates have the form of at least substantially rectangular test strips.

It should be understood that the terms test substrate and test strip as used herein may include not only the actual test strip material but also a casing or housing in which a test substrate or test strip is provided. Thus, the test strip receiving structure of the systems of the invention may be sized and configured to receive the test strip in whatever form, with or without a housing, in which the test strip is ordinarily used. It should also be recognized that while the overall dimensions of a test strip may have one shape, the actual substrate material on which a sample is interrogated may have another shape. For example, a rectangular test strip may have one or more square, circular or oval sample deposition substrates along its length.

The tests strips may include a surface enhance Raman spectroscopy SERS-active surface, such as a roughened metallic surface, for deposition and analysis of a sample by irradiation of the sample deposition area of the strip and/or the test strips may be lateral flow binding assay type test strips and Raman interrogation may occur at one or more antigen binding stripes and control stripes. U.S. Pub. No. 20060240401 (application Ser. No. 11/340,712) and U.S. Pub. No. 20060166302 (application Ser. No. 10/905,956) disclose SERS substrate type Raman test strips and uses thereof, and are each incorporated by reference herein in their entireties. Copending U.S. application Ser. No. 60/765,699 discloses the use of lateral flow type test strips with Raman spectroscopy, and is incorporated by reference herein in its entirety.

Non-Lateral Flow Embodiments

In embodiments of the invention that do not depend on lateral flow of a mobile analyte-binding phase but instead are based on directly irradiating a deposited sample, the test substrate, such as a test strip, provides an area to deposit a body fluid sample onto which the laser radiation is directed, and even more preferably, includes features to enhance spectroscopy. In one embodiment, the test strip can include a substance for surface enhanced Raman spectroscopy (SERS), such as a roughened metallic surface and/or SERS-active metallic particles. The SERS-active metallic particles may, for example, be solid metallic particles or particles that are at least partially coated with a SERS-active metal.

SERS techniques enhance Raman spectroscopic signals and allow more effective differentiation of spectroscopic signatures by placing the sample to be analyzed in contact with SERS material (usually an appropriately prepared metal surface). While not being limited by theory, two mechanisms are considered responsible for the improvement. The primary contribution is an enlargement of the local electromagnetic field, due to the excitation of a localized surface plasmon, while the other mechanism results from a charge transfer-state between the surface complex of the adsorbed molecule and the metal surface.

Figure 7:
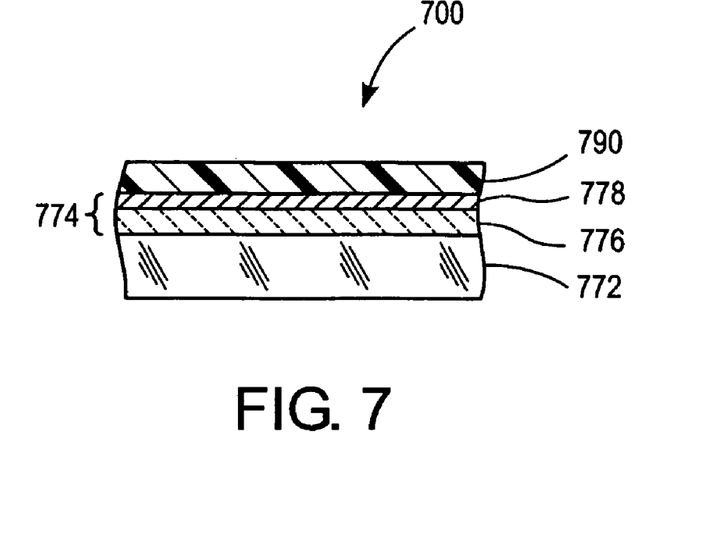
FIG. 7 shows an example of a SERS substrate-type test strip.

A SERS test strip includes SERS-active material, such as, for example silver, gold, nickel, copper and/or cadmium. FIG. 7 illustrates one exemplary embodiment of SERS active test strip 700 (non-lateral flow type) including a support substrate 772 and a roughened metal surface including layer 774 having a degree of roughness sufficient to induce the SERS effect. Layer 774 may include a microparticle or microstructure layer 776 on the upper surface of support substrate 772 and/or a metal layer 778 containing silver, gold, nickel, copper and/or cadmium.

In one embodiment, a coating 790 can be applied to roughened surface layer 774 to sorb analytes (absorb and/or adsorb) which are not easily sorbed by the roughened surface, but which are capable of either penetrating into the coating or being attached to the coating. The analytes are thereby absorbed and/or adsorbed to coating 790 and become positioned in the vicinity of the roughened surface and exhibit the SERS effect. The coating may be specific or non-specific for the analyte so long as it provides the sorbing function.

In one embodiment, the SERS active material is positioned only in target (sample deposit) area of the test strip. In use, a sample is deposited on the SERS-active material in the target area and light is directed toward the sample for spectroscopic analysis. The deposited sample may be unprocessed or further processed before the irradiation. For example, where the target zone is coated with one or more analyte-specific antibodies, the target zone may be washed with a buffer solution prior to irradiation to remove non-specifically binding components of the sample from the target zone. A person of skill in the art will appreciate that the choice of SERS-active material will depend on the desired analyte and the chosen radiation spectrum. In one embodiment, the SERS-active materials include a porous sol-gel containing gold microcolloid particles where the laser radiation is about 785 nm. SERS techniques and materials are, for example, described in U.S. Pat. Nos. 5,400,136 and 5,864,397, each of which is incorporated herein by reference in its entirety.

In another embodiment, the test substrate, such as test strip, additionally includes a lancet, which can puncture a user's skin, typically on the user's finger, to draw a blood sample. The lancet may include a sharpened tip and a mechanism for propelling the metal tip into a user's skin. An exemplary lancet is the BD Ultra-Fine™ Lancet available from BD Consumer Healthcare (Ontario, Canada).

Lateral Flow Test Strip Embodiments

One aspect of the present invention provides a method to read lateral flow immunoassay test kits quantitatively for the amount of one or more preselected antigens (or antibodies) present in the sample, using Raman spectroscopy. For example a Raman spectrum or part thereof may be analyzed from the test stripe and optionally also from a control stripe of an hCG (human chorionic gonadotropin) lateral flow immunoassay pregnancy test kit, such as the AccuClear hCG pregnancy test kit (Inverness Medical Innovations, Inc.). The Raman peaks at the test stripe (which is seen visually as a reddish stripe on the strip) are unique to the gold antibody conjugate, and the peak heights are directly proportional to the concentration of the captured gold complex. The Raman peak heights provide a quantitative readout either as a direct reading of the analyte peak intensity or as a ratio to either the Control stripe or to an additional Raman feature on the strip. The concentration of an analyte in a sample may, thus, be determined.

The gold particles of the bead-antibody conjugate may enhance the Raman signal by the SERS effect. Whether or not the present invention is implemented for surface-enhanced or natural scattering intensity, it relies on the Raman signature of the analyte-binding complex (such as bead-antibody complex) without the addition of a special Raman label. Using control reagents a concentration calibration may be readily produced for comparison with the observed Raman peak intensities. Also, since the size of the gold particles can be controlled when preparing the gold conjugates, a size may be chosen to optimize the Raman effect for quantification. The present invention may also utilized beads of material other than gold. For example, beads made of other SERS-active materials such as silver, nickel, copper and/or cadmium may be used. SERS-active metallic particles may, for example, be solid metallic particles or particles that are at least partially coated with a SERS-active metal. SERS techniques and materials are described in U.S. Pat. Nos. 5,400,136 and 5,864,397, which are incorporated herein by reference in their entirety.

A Raman spectroscopy system of the invention may, for example, be used with an AccuClear hCG (human chorionic gonadotropin) test kit by measuring either the peak intensity directly (after a suitable calibration run) or by ratioing the Raman peak intensities at the T (test) and C (control) positions on the test kit after the liquid sample has been allowed to flow laterally though the kit.

One embodiment of the invention provides a test strip (that may be a lateral flow test strip or non-lateral flow test strip) assay that is notched, has other physical elements and/or is marked to permit the operative alignment of the test strip with respect to the test strip receiving structure of the Raman spectroscopy system. For example, for a lateral flow assay test strip, the test strip may be notched, have other physical elements and/or be marked to permit the operative alignment of the test strip with respect to the test strip receiving structure of the Raman spectroscopy system so that the test and/or control stripe(s) regions can be read. For example, the marking and/or notch(es) may be in register with the stripes or they can be offset from the stripes so long as the probe of the Raman reader unit is suitably positioned (coordinated) to read a/the strip when the mark or notch is correctly positioned. A related embodiment provides a Raman reader that includes a test strip receiving member adapted to align, or allow the alignment of, the test stripes with illuminating and signal receiving elements of the Raman spectrometer based on a reference marking and/or notch(es) present on a lateral flow assay test strip. A still further embodiment provides a system that includes the aforementioned test strip and a Raman reader unit that are adapted to be used together. The lateral flow matrix (material) may or may be at least partially housed in a casing. In this case, the casing, rather than the actual strip material may include one or more reference markings, notches and/or other physical elements that permit the strip to be properly aligned in the reader for reading of the stripe(s).

Figure 8:
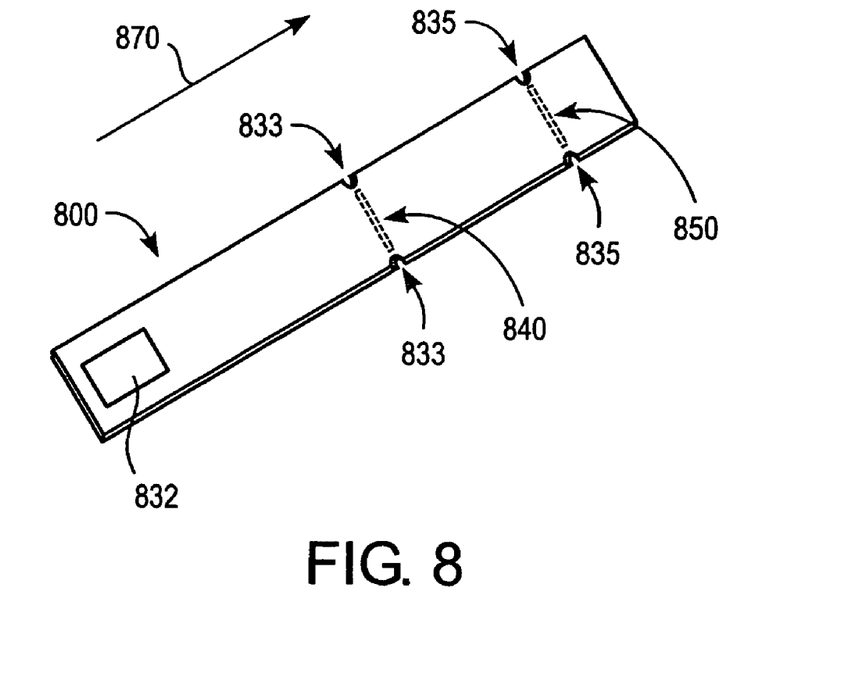
FIG. 8 shows a lateral flow assay test strip having notches for aligning the test stripe and control stripes of the strip with the optical probe of a Raman reader unit.
Figure 9:
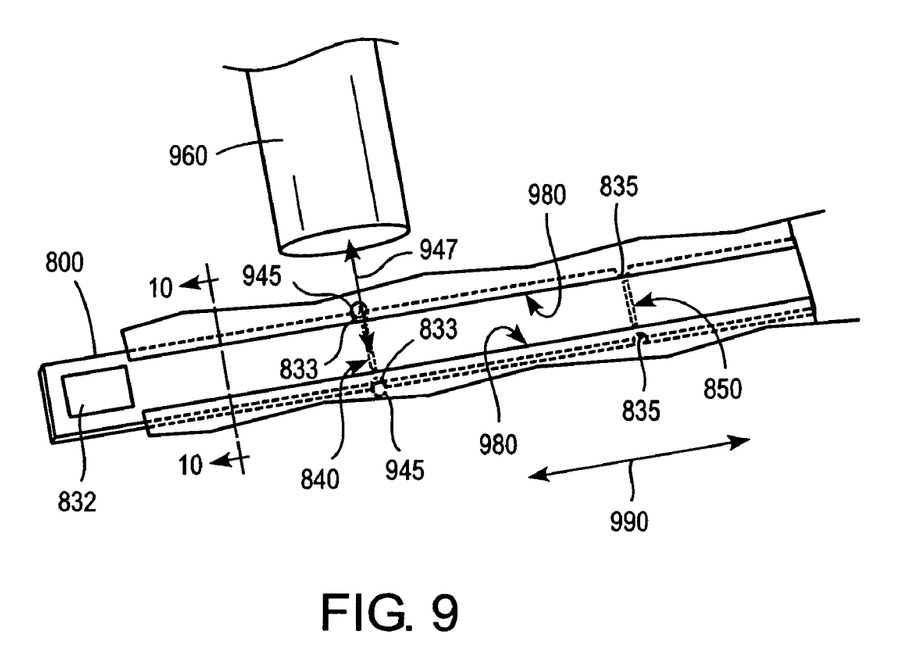
FIG. 9 shows the lateral test strip of FIG. 8 alignedly positioned in the positioning mechanism of a Raman reader unit for reading of the test stripe by the optical probe of the reader unit.
Figure 10:
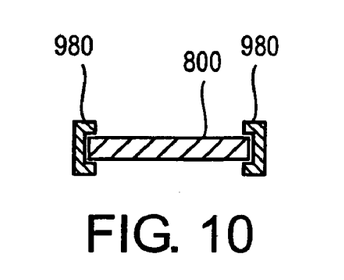
FIG. 10 shows a cross section of the test strip of FIG. 9 positioned in the test strip-guiding rails of the reader unit.

For example, FIG. 8 shows a lateral flow assay test strip 800, having a sample deposition area 832 and bilateral notches 833 formed at the axial position of a test stripe 840 and bilateral notches 835 formed at the position of a control stripe 850. Arrow 870 illustrates the direction of lateral flow in the test strip. FIG. 9 shows an example of the test strip of FIG. 8, positioned in a strip-positioning mechanism of a Raman reader apparatus. Lateral protrusions 945 of the reader align with notches 833 of the test strip so that the strip clicks into position for reading of test stripe 840 (as currently shown) or control stripe 850 by the Raman probe 960 to illuminate the stripes and collect resulting Raman scattered light therefrom, along optical path 947. The test strip 800 and/or protrusions 945 may have sufficient give or springiness so that the test strip can be clicked from one alignment position into another by an operator. Guide rail "tongues" 980 of the reader unit overlay the edges of the test strip and collectively form a slot in which the test strip is guided. Arrow 990 shows the lateral direction in which the test strip can be moved forward and backwards. In one embodiment, the Raman reader unit prompts the operator to position the test strip at one or more test stripes and/or control stripes. FIG. 10 shows a cross sectional view, along line 10 of FIG. 9, of the test strip positioned in the test strip-guiding rails of the reader unit.

Raman intensity (peak height) is directly proportional to the concentration of a scatterer. Accordingly, the concentration of an analyte may, for example, be determined by multiplying the Raman intensity at a wavenumber or wavenumber band associated with the Raman scattering of the bead-bound analyte-binding element (which may be an antibody), or a complex or the analyte-binding element and analyte, at the test stripe for the analyte, with a proportionality constant, which may, for example, be determined in advance using control samples having known concentrations of a subject analyte. For embodiments in which the test strip also includes a control stripe, a ratio of Raman signal readings from the test stripe and control stripes may, for example, be multiplied with a proportionality constant to obtain the desired analyte concentration. Using such a ratio advantageously corrects for potential calibration variabilities that may arise with the Raman reader unit.

With respect to lateral flow binding assay test strips, Antibodies used as binding elements may be of any suitable form or type, may be produced by any method, and may be unprocessed or processed, for example proteolytically into FAb fragments.

Fluid and liquid samples that may be assayed according to the invention include, but are not limited to, blood, urine and saliva. Other body fluids that may be assayed include, for example, lymph and cerebrospinal fluid. Body fluids that are assayed may be unprocessed ("raw"), such as blood, or processed, such as plasma. Semi-fluids such as sputum or fecal matter may also be assayed. Non-fluid or semi-fluid samples may be also fluidized or further fluidized for assay according to the invention. The systems and methods of the invention advantageously may also be used to evaluate non-body fluid biological samples and non-biological samples using test substrates such as test strips.

Multiple Analyte Analysis

The systems of the invention may advantageously be used to quantitatively and/or qualitatively analyze multiple analytes within a body fluid sample or other type of sample. This aspect of the invention is further described below with reference to body fluid samples, such as blood samples.

Where the device of the present invention investigates multiple analytes within a single sample during a single analysis it may be particularly advantageous to test analytes related to a single condition of interest. For example, when a patient arrives for a check-up, instead of running two diagnostic tests related to one condition, e.g., one for blood sugar, one for hemoglobin A1c, the present invention allows simultaneous testing. The result is a cost effective and almost immediate analysis. Thus, one embodiment of the invention provides for the analysis of multiple analytes that are related to a single preselected condition or to the health status of a preselected organ or tissue system.

Other groups of analytes can include a blood chemistry profile. For example, a test or evaluation for levels of two or more of: urea (blood urea nitrogen, "BUN"), creatinine, uric acid, bilirubin (e.g., total and/or direct bilirubin), phosphorous, alkaline phosphatase (alk. P-Tase), total protein, albumin, globulin, glucose, carbon dioxide, T-3, T-3 uptake, T-4, free thyroxine index, TSH, free T-4, cholesterol, triglycerides, HDL, LDL, VLDL, iron, iron saturation, total iron binding and ferritin may be performed.

In another embodiment, assessments may be desirable to reveal the levels of beneficial and toxic chemical entities that commonly occur in humans as the result of lifestyle and toxic exposures. Such a test may be desirable for persons concerned with health hazards in their living or work space.

In yet another embodiment, analytes may be chosen which focus on a certain preselected health condition. For example, testing for analytes related to cardiac health may be desirable during a regular check-up or as part of a heart health screening. Such analytes may, for example, include two or more of cholesterol (e.g., total, LDL, and/or HDL), triglycerides, C-reactive protein (CRP), brain natriuretic peptide (BNP), troponin, myeglobin and homocysteine.

In an additional embodiment, it may be desirable to screen for a group of drugs, and in particular illegal drugs or drugs of abuse, such as but not limited to narcotics, amphetamines and hallucinogens. As an example, analytes could include two or more of marijuana (including but not limited to active substance THC), amphetamines, methamphetamines, barbiturates, benzodiazepines, cocaine, 3,4-methylenedioxymethylamphetamine (MDMA), opioids (such as but not limited to morphine, heroin and synthetic opioids), D-lysergic acid N,N-diethylamide (LSD) and 1-(1-phenylcyclohexyl)piperidine (PCP).

The Raman spectroscopy systems of the invention may be used to monitor pharmacotherapy in human or animal subjects. The quantification of a preselected drug and/or its metabolites in a sample obtained from a patient may be used to determine whether the active species of the drug is/are present at a desired concentration in the patient, and if not, the cause of the problem. The activity of many therapeutic drugs is at least partially dependent on their metabolism to one or more active forms within the body. For example, buproprion (Zyban™, Wellbutrin™) is extensively metabolized into three active metabolites. Activity of the antihypertensive angiotensin I-converting enzyme (ACE) inhibitors benazepril, enalapril, moexipril, and quinapril is due to the active metabolites benazeprilat, enalaprilat, moexiprilat, and quinaprilat, respectively. The antihistamine terfenadine is metabolized to an active metabolite fexofenadine. Determining the relative concentration of parent drug to active metabolite(s) in a patient, according to the invention, provides an indication of whether drug metabolism is normal and/or whether an abnormality in metabolism that interferes with the pharmacotherapy may be present, for example due to a metabolic insufficiency in the patient. Determining the concentration(s) of parent drug and/or metabolites thereof in a patient can provide information as to whether there is a problem in drug absorption/administration or a patient's compliance therewith, if the desired level of drug or metabolites is not achieved. Therapeutic drugs that may be monitored and/or evaluated for metabolism according to the invention include, but are not limited to: anti-arrhythmics such as digoxin and quinidine; antibiotics such as vancomycin, gentamicin, tobramycin, amikacin and netilmycin; anti-epileptics such as phenytoin, phenobarbital, carbamazepine, and ethosuximide; anti-asthmatics such as theophylline, and anti-rejection drugs such as cyclosporine.

The results determined by a microprocessor of the system can be displayed on a display device. Depending on the particulars of the analyte and the user's needs, the displayed results can be provided in a variety of forms. For example, where glucose is tested, the results can be displayed quantitatively (120 mg/dl) or relatively (Normal). With other analytes, it may be desirable to display results indicating only the presence (or absence) of an analyte (e.g., the presence of poisons).

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

What is claimed is:

1. A Raman spectroscopy system comprising:
   an input fiber through which radiation can propagate to irradiate a sample;
   a collection fiber through which radiation scattered by the sample can be coupled to a detector;
   an optical head assembly defining an input path and an output path,
   wherein the input path comprises at least one light directing element that receives excitation radiation from the input fiber and directs it to the sample and the output path comprises at least one light collecting element that collects radiation scattered by the sample and couples the scattered radiation into the collection fiber; wherein the input and output paths of the head assembly are at least substantially orthogonal and
   the head assembly further comprises a dichroic mirror that directs the excitation radiation to the sample by reflection and transmits scattered radiation returning from the sample to the output path; and
   a fluid sample test substrate receiving structure sized and configured for receiving a body fluid sample test substrate and positioning said substrate for optical interrogation via the optical head assembly,
   wherein the fluid sample test substrate is a test strip, and
   wherein the test strip is a lateral flow binding assay test strip.

2. A method for evaluating a body fluid sample by Raman spectroscopy, comprising the steps of:
   depositing a body fluid sample on a test strip;
   inserting the test strip into a Raman spectroscopy system, the system comprising:
      an optical assembly defining an input path and an output path,
      wherein the input path comprises at least one light directing element that receives excitation radiation from a light source and directs it to a sample and the output path comprises at least one light collecting element that collects radiation scattered by the sample for analysis, wherein the input and output paths of the optical assembly are at least substantially orthogonal, and
      the optical assembly further comprises a dichroic mirror that directs the excitation radiation to the sample by reflection and transmits scattered radiation returning from the sample to the output path; and
      a fluid sample test substrate receiving structure sized and configured for receiving a body fluid sample test substrate and positioning said substrate for optical interrogation via the optical assembly;
   wherein the body fluid sample test substrate receiving structure is a test strip-receiving structure;
   the system irradiating at least one part of the test strip to generate a Raman spectra; and
   the system analyzing at least part of the Raman spectra;
   wherein the test strip is a lateral flow binding assay test strip comprising a mobile phase and one or more test stripes and optionally one or more control stripes, and the system irradiates one or more test stripes and optionally one or more control stripes of the test strip.

3. The method of claim 2, wherein the mobile phase comprises SERS-active particles.

4. The method of claim 3, wherein the SERS-active particles comprise one or more of gold beads or gold-coated beads.

* * * * *